United States Patent [19]
Brovold

[11] Patent Number: 5,817,946
[45] Date of Patent: Oct. 6, 1998

[54] GYRATORY COMPACTION APPARATUS FOR CREATING COMPRESSION AND SHEAR FORCES IN A SAMPLE MATERIAL

[75] Inventor: Thomas Emil Brovold, Chaska, Minn.

[73] Assignee: Test Quip, Inc., Chaska, Minn.

[21] Appl. No.: 739,007

[22] Filed: Oct. 28, 1996

[51] Int. Cl.$^6$ .............................. G01N 3/08; G01N 3/24
[52] U.S. Cl. ................................................ 73/818; 73/843
[58] Field of Search ............................. 73/38, 84, 432.1, 73/789, 790, 794, 795, 806, 808, 811, 813, 815, 816, 818, 842, 843, 845; 425/169, 411, 415, 421

[56] References Cited

U.S. PATENT DOCUMENTS

| | | |
|---|---|---|
| 2,972,249 | 2/1961 | McRae et al. . |
| 4,942,768 | 7/1990 | McRae . |
| 5,036,709 | 8/1991 | McRae . |
| 5,275,056 | 1/1994 | Hamilton et al. .......................... 73/794 |
| 5,323,655 | 6/1994 | Eagan et al. ............................ 73/432.1 |
| 5,456,118 | 10/1995 | Hines et al. . |

*Primary Examiner*—George M. Dombroske
*Assistant Examiner*—William L. Oen
*Attorney, Agent, or Firm*—Gregory F. Cotterell

[57] ABSTRACT

The present invention contemplates a gyratory compaction apparatus for creating compression and shear forces in a sample material, the apparatus using a single roller to accomplish the gyration comprising a hollow cylinder mold including first and second end plates in slidable engagement with the mold at respective first and second open ends, with a chamber inside the mold for receiving the sample material, a support frame having an interior suitable for receiving the mold therein, a compression mechanism for compressing the sample material, and a gyratory assembly comprising a rotational drive motor having a drive shaft aligned along the longitudinal axis of the support frame interior, a cam mounted at the end of the drive shaft, a gyratory plate having an inner housing for encompassing and operably engaging the cam including a spring biased plunger operably engaging the cam and a first outer angular contact bearing for operably engaging the mold inner surface and a driven plate operably mounted to the support frame with a second angular contact bearing and operably coupled to the gyratory plate with a pin mounted eccentric to the longitudinal axis of the cylindrical interior and an annular planar thrust bearing concentric to the pin so that when the cam is driven in a first direction the gyratory plate is rotated concentrically about the longitudinal axis of the cylindrical interior and when the cam driven in an opposite second direction, the cam engages the plunger pivoting the gyratory plate about the axis of the pin radially displacing the gyratory plate and first angular contact bearing so that the gyratory plate rotates eccentric to the longitudinal axis while the first angular contact bearing tilts the mold to a specified angle relative to the longitudinal axis of the housing and gyrates the mold about the specified angle while the sample material is compressed within the mold.

20 Claims, 6 Drawing Sheets

5,817,946

GYRATORY COMPACTION APPARATUS FOR CREATING COMPRESSION AND SHEAR FORCES IN A SAMPLE MATERIAL

FIELD OF THE INVENTION

This invention relates generally to devices for testing materials, more specifically to a device for accomplishing compaction while gyrating the specimen container and in a specific instance relates to a portable gyratory compactor for the testing of specimens of asphalt paving materials.

BACKGROUND OF THE INVENTION

In the general field of materials testing, a number of different types of material mixtures are amenable to testing by subjecting specimens of the material to compressive forces while concomitantly imposing shear forces on the mixture and then measuring the degree of compaction the specimen undergoes in response to the compression and shearing. As an example, such testing has been found to be useful in measuring asphalt mixture samples in the evaluation of the asphalt mixture used in paving road surfaces as a measure of the quality of the road surface.

An asphalt paving mixture generally comprises a crushed rock aggregate, a bituminous binder, and air voids. Because the individual particles of rock constituting the aggregate are irregular in shape and size, when initially mixed, there are numerous small air voids in the mixture. The strength, durability and cost of asphalt pavement are directly related to the type and size of the particles of rock found in the aggregate, the proportion of binder in the aggregate and the amount of air voids in the final pavement after it has been rolled out, along with other factors. Too much bituminous binder, for instance, under compression fills in substantially all of the air voids and causes flowing of the asphalt mixture in response to the compressive forces which eventually leads to early deterioration of the road surface. Too little bituminous binder can leave the road surface brittle and porous, subjecting the surface to cracking and susceptible to freeze-thaw disruption with the entry of water for roads situated in those climates subjected to freezing temperatures.

The purpose of gyratory compaction testing is to subject a sample of the asphalt mixture to compression and shear forces to determine the degree of compaction achievable which is directly related to the amount of bituminous binder and air voids present in the asphalt mixture. Known test parameters are the density of the aggregate, bituminous binder, and weight of the sample. The degree of compaction is then used to calculate the change in density due to compaction of the sample during the test run. The results are then useful to determine whether a particular asphalt paving mixture will have the strength and durability required for the anticipated traffic conditions on a particular roadway before the asphalt is applied to the roadway.

The United States Department of Transportation Federal Highway Administration Publication No. FHWA-SA-95-003, Background of Superpave Asphalt Mixture Design and Analysis (February 1995) describes a gyratory compaction test for asphalt paving material and the conclusions which may be inferred from gyratory compaction testing. Devices for performing these tests have been developed by Troxler Electronic Laboratories, Inc., Pine Instrument Company and others.

These guidelines call for precise, reproducible compressive forces, angles of gyration and specified temperatures for testing a sample within the mold. It is a combination of the compressive force and angle of gyration that determines the resultant shear force placed on the specimen. Precise control of compression and angle of gyration is critical in obtaining accurate test results that are reliable in predicting the actual conditions of density, alignment of aggregate and appropriate elastic properties within the asphalt mixture. The proper temperature is also critical in maintaining the appropriate viscosity of the sample during the test so as to approach similar to actual conditions during the paving procedure.

In general, the testing protocol requires that a heated and pre-weighed specimen of the asphalt paving mixture be placed in a cylindrical mold. The specimen is then compressed to a predetermined pressure and an initial density calculation is determined. Since the density of the rock and bituminous binder are known, the measured density, in conjunction with the known values of two of the components, is used to calculate the percentage of air voids in the sample. The specimen mold is then moved in a gyratory fashion at a small angle relative to, and around, the long axis of the compressive force as applied to the sample through mold end plates while the sample is kept under a specified amount of compression. The compression force and the gyratory motion of the mold combine to produce a shear stress in the specimen as long as at least one of the end plates remains perpendicular to the longitudinal axis of the compressive force. This gyratory compaction testing is designed to reproduce the shear stresses induced in the asphalt mixture when it is laid down and undergoes vibratory compression from the paving rollers. As noted above, it is the resulting compacted paved asphalt that will determine the quality of the road surface.

This shear stress causes individual particles of rock to move, realign and perhaps even to break, thus filling a substantial amount of the voids and reducing the volume of the paving mixture in the mold. The strength, durability, elasticity and thus the suitability of the paving mixture for anticipated traffic conditions is inferred from the reduction in volume, and therefore, change in density of the specimen and other observations made during the test.

The principles of gyratory compaction testing are more fully explained in the above-referenced publication. However, if the gyratory compaction test is to be precise and reliable, the compression force and the angle at which the mold cylinder is inclined as it is gyrated must be held constant within a very narrow range. Generally, maintaining the angle of inclination precisely within the narrow range specified by the testing protocol is far more difficult than maintaining the compressive force within the specified range.

U.S. Pat. No. 2,972,249 issued to McRae, et al., discloses a gyratory compactor device that holds the specimen within a mold chuck between two opposed compression rams. Shear forces are generated by gyrating the mold chuck around the long axis of the compression rams. The mold is gyrated using multiple rollers mounted in a chuck mold oscillator frame, the wheels being offset in relation to each other and engaging a flange on the outside of the chuck mold.

U.S. Pat. No. 5,456,118 issued to Hines, et al., also discloses a gyratory compactor that accomplishes gyration by tilting the mold. This disclosure uses an external mold carriage assembly attached to a rotatable circular base below and a carriage tilt link assembly above. Just as with the McRae device, multiple rollers engage an outside flange rim of the mold and spin around the outside of the mold in a plane tilted to the axis of the compression ram. A secondary consequence of this device is the lateral moment arm of force exerted on the compression ram as the mold and contents are gyrated. Any deflection in the shaft of the compression ram shaft towards the induced tilt axis decreases the amount of shear forces on the sample and changes the testing environment. The amount of lateral moment arm force on the compression ram shaft is not reproducible from test to test. The Hines device also requires the removal of the mold from the tilting assembly to facilitate loading and extracting the test sample. This severely curtails the number of samples that can be run over time because the device requires realignment and recalibration for each run and the mold must be brought back to testing temperature before the next test run.

U.S. Pat. Nos. 4,942,768 and 5,036,709 issued to McRae disclose a gyratory compactor that tests a specimen held in a mold by a chuck. The chuck, not the mold, is then gyrated using a spinning offset roller assembly engaging a flange to the outside of the chuck as the specimen is compressed from the bottom while held in a stationary mold. Gyration of the chuck and its end plate in contact with the specimen effects a kneading action on the specimen within the mold. As with the prior two devices mentioned above, this device uses a bulky assembly, with multiple rollers, spinning to the outside of the specimen mold to accomplish the gyration.

These gyrating assemblies have resulted in testing machines that are large, heavy and therefore not transportable. Their expense substantially influences, and limits, the number of machines available, increasing the likelihood that large mixtures of asphalt will be paved out having never been tested for appropriateness of use. These gyratory inducing mechanisms, using multiple rollers outside the mold against one or more flanges also to the outside, require many moving parts held in a large framework and cabinet.

At the conclusion of the gyratory compaction test, the specimen must be stripped from the mold. The Hines and earlier McRae machines discussed above require that the mold be removed from the machine and inserted onto another device where the specimen is pressed out of the mold. These machines must be precisely readjusted every time a sample is run to maintain the angle of inclination because the entire setup has to be taken down and reassembled between test runs. Additional time is lost bringing the mold back up to temperature before the next sample can be run in that mold. While they are suitable for laboratory use, those machines are not readily adaptable for mobile operation and testing samples of paving mix at the point of mixing or at the job site.

Consequently, there is a need for a simple, lightweight gyratory compaction testing machine which controls compression forces and maintains the angle of inclination precisely with minimal adjustment and which may be readily mounted on a van, truck or other vehicle and operated at the site where the asphalt is mixed and/or the roadway is being paved. There is a need for a gyratory testing machine which can strip the specimen from the mold without removing the mold from the gyratory compaction testing machine.

SUMMARY OF THE INVENTION

Material testing is a broad area and encompasses a number of types of tests which include shearing and compaction. The above referenced United States Department of Transportation Federal Highway Administration test is a specific example of a testing protocol to be used on asphalt that is to be laid and rolled in forming a road surface. In brief, the test requires an approximately eight pound sample of the asphalt, held at 300° F., to undergo compaction at 600 Kpa and shear stress generated by a gyratory tilting at an angle of 1.25°±0.025. Additionally the sample must be held between two end plates that remain parallel to each other during the testing. In order to accumulate test data that is meaningful under conditions that are reproducible, a gyratory compactor must conform to high standards of precision and reliability.

The present invention contemplates a gyratory compaction apparatus for creating compression and shear forces in a sample material, the apparatus using a single roller acting within a cylinder mold to accomplish the gyration. The apparatus comprises a hollow cylinder mold open at both ends and includes a first and second end plates in slidable engagement within the mold at respective first and second open ends. These plates in conjunction with the mold creates a chamber between the end plates for receiving the sample material. A support frame is provided that defines a hollow cylindrical interior suitable for receiving the mold therein. A compression mechanism, mountable on the support frame, is used to compress the sample material. The compression mechanism includes a rod aligned along a longitudinal axis of the cylindrical interior and operably engages the first end plate. A gyratory assembly, removably mountable between the support frame and mold and engageable with the second end plate comprises a rotational drive motor for reversibly rotating the gyratory assembly which has a drive shaft proximate the second open end and aligned along the longitudinal axis of the cylindrical interior. There is a cam mounted at the end of the drive shaft along with a gyratory plate having an inner housing for encompassing and operably engaging the cam which includes a spring biased plunger operably engaging the cam. A first angular contact bearing is mounted to the cam plate for rollably engaging a mold inner surface proximate the second open end. A driven plate is operably engageable with the support frame through a second angular contact bearing and operably coupled to the gyratory plate with a pin mounted eccentric to the longitudinal axis of the cylindrical interior. There is an annular planar thrust bearing between the gyratory plate and driven plate concentric to the pin so that when the cam is driven in a first direction the gyratory plate is rotated concentrically about the longitudinal axis of the cylindrical interior and when the cam is driven in an opposite second direction, the cam engages the plunger pivoting the gyratory plate about the axis of the pin so that the gyratory plate rotates radially relative to the longitudinal axis and now rotates eccentrically around the longitudinal axis. The first angular contact bearing thus tilts the mold to a specified angle relative to the longitudinal axis of the cylindrical interior and gyrates the mold about the specified angle while the sample material is compressed within the mold.

A preferred embodiment of the present invention for a gyratory compactor apparatus for subjecting a material sample to controlled shear and compaction forces comprises a hollow cylindrical housing having an inner cylindrical wall, a bottom and a removable top. There is a first angle rim mounted on the bottom surface within the cylinder concentric to the inner cylindrical wall and having a frusto-conical outer surface. A second angle ring is adjustably mounted to the inner cylindrical wall having a frusto-conical inner surface and is concentric to the inner cylindrical wall, the inner surface is substantially parallel to the first angle rim outer surface and has an overall inner diameter greater than an overall outer diameter of the first angle rim. A hollow mold cylinder open at both ends for placement within the housing, has an inner and an outer mold surface and rounded first and second ends. The first rounded end is suitable for resting on the angled outer surface of the first angle rim. The mold cylinder is tiltable on the first angle rim and provides for the second rounded end to engage the angled inner surface of the second angle ring. The mold is completed using a removable first end plate and a removable second end plate, both end plates in slidable engagement with the mold inner surface, the inner mold surface and both end plates defining a volume suitable for receiving the material sample. A motor is mounted to the top and includes a drive shaft projecting into the housing through a hole in the top centered along the longitudinal axis of the housing. A compression cylinder and rod are mounted to the housing bottom with the rod projecting into the housing through a hole in the bottom centered along the longitudinal axis of the housing, the rod operably engaging the first end plate. A controller subsystem is operably connected to the motor and compression cylinder for controlling the motor and compression cylinder. A gyratory assembly, operably attached on an inner surface of the top, comprises a cam, a cam plate, a gyratory plate, a first angular contact bearing, and a second angular contact bearing. The cam is mounted at the end of the drive shaft. The gyratory plate has an inner housing for encompassing and operably engaging the cam and includes a spring biased plunger operably also engaging the cam. The first outer angle contact bearing for operably engaging the mold inner surface fits over the cam plate. The driven plate is operably mounted to the top with the second angular contact bearing and operably coupled to the gyratory plate with a pin mounted eccentric to the long axis of the housing. There is included an annular thrust bearing concentric to the pin so that when the cam is driven in a first direction the gyratory plate is turned concentrically about the longitudinal axis of the housing and when the cam is driven in an opposite second direction, the cam engages the plunger pivoting the gyratory plate about the axis of the pin so that the gyratory plate moves radially from the longitudinal axis of the housing and spins eccentrically around the longitudinal axis. The first angular contact bearing, riding on the cam plate, also moves radially with the gyratory plate and tilts the mold to operably engage the second angle ring at a specified angle to the longitudinal axis of the housing and gyrate the mold about the specified angle while the sample material is compressed within the mold.

A general object of this invention is to provide an apparatus which holds a cylindrical mold at a precise angle of inclination while the mold is gyrated. Accordingly, the invention constrains the mold between two parallel structures as the mold is gyrated. Thus the cylindrical mold maintains a precise angle of inclination even though the mold may be displaced along its longitudinal axis as the mold is gyrated.

An additional object of the invention is to provide a simple mechanical means to align the parallel structures and thus insure that the apparatus can accommodate cylindrical molds which vary slightly in length, outer diameter, eccentricity and other physical characteristics and still maintain the precise angle of inclination required by the gyratory compaction testing procedure.

A further object of the invention is provide a gyratory compaction testing apparatus in which the gyratory motion of a cylindrical mold is produced by forces acting on the inner surface of the mold, and more particularly by the eccentric rotary motion of a component of the apparatus which engages the inner surface of the mold and forces the mold cylinder into positive contact with the parallel structures which hold the mold in alignment at the desired angle of inclination as the mold cylinder is gyrated.

An additional further object of the invention is to provide a combination of bearings which enable the rotating components of the apparatus simultaneously to withstand compressive forces directed along a central axis of rotation, rotate freely about the central axis of rotation, and permit one of the rotating components to move radially, away from the central axis of rotation, thus rotating in an eccentric manner about the central axis of rotation to gyrate the mold.

Another object of the invention is to provide a means for extracting the specimen from the cylindrical mold at the conclusion of the gyratory compaction test procedure without removing the mold from the apparatus.

Another further object of the invention is to provide a gyratory compaction testing apparatus which is safe, simple, light in weight, rugged and readily adaptable to mobile operation.

Other objects of the present invention and many of the attendant advantages of the present invention will be readily appreciated as the same become better understood by reference to the following detailed description when considered in connection with the accompanying drawings.

DETAILED DESCRIPTION OF THE INVENTION

Figure 1:
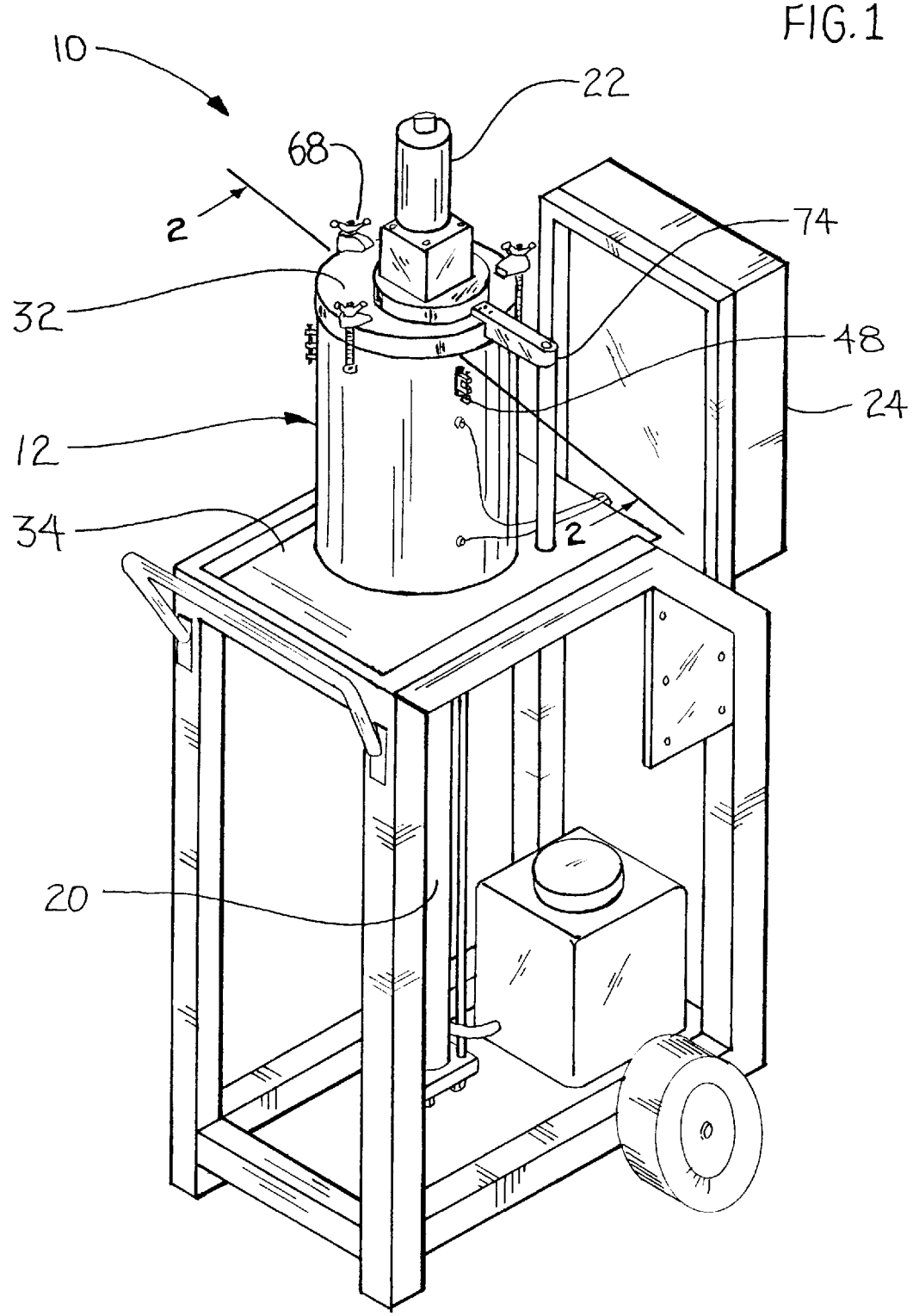
FIG. 1 is a perspective view of an embodiment of the present invention.

In reference to FIGS. 1 through 4, wherein like numbers refer to like components throughout the Figures, there is disclosed a gyratory compactor apparatus 10 comprising a cylinder housing 12, a mold cylinder 14, a first angle rim 16, a second angle adjustment rim 18, a hydraulic cylinder 20, a motor 22, a gyratory compaction control module 24, and a gyratory assembly 26.

Cylinder housing 12 further includes a housing wall 30, a lid or top 32, and a base plate or bottom 34. Top 32 includes a hole 33 concentric to the longitudinal axis of housing wall 12. Bottom 34 includes a hole 58, also concentric to the longitudinal axis of housing wall 12.

Figure 2:
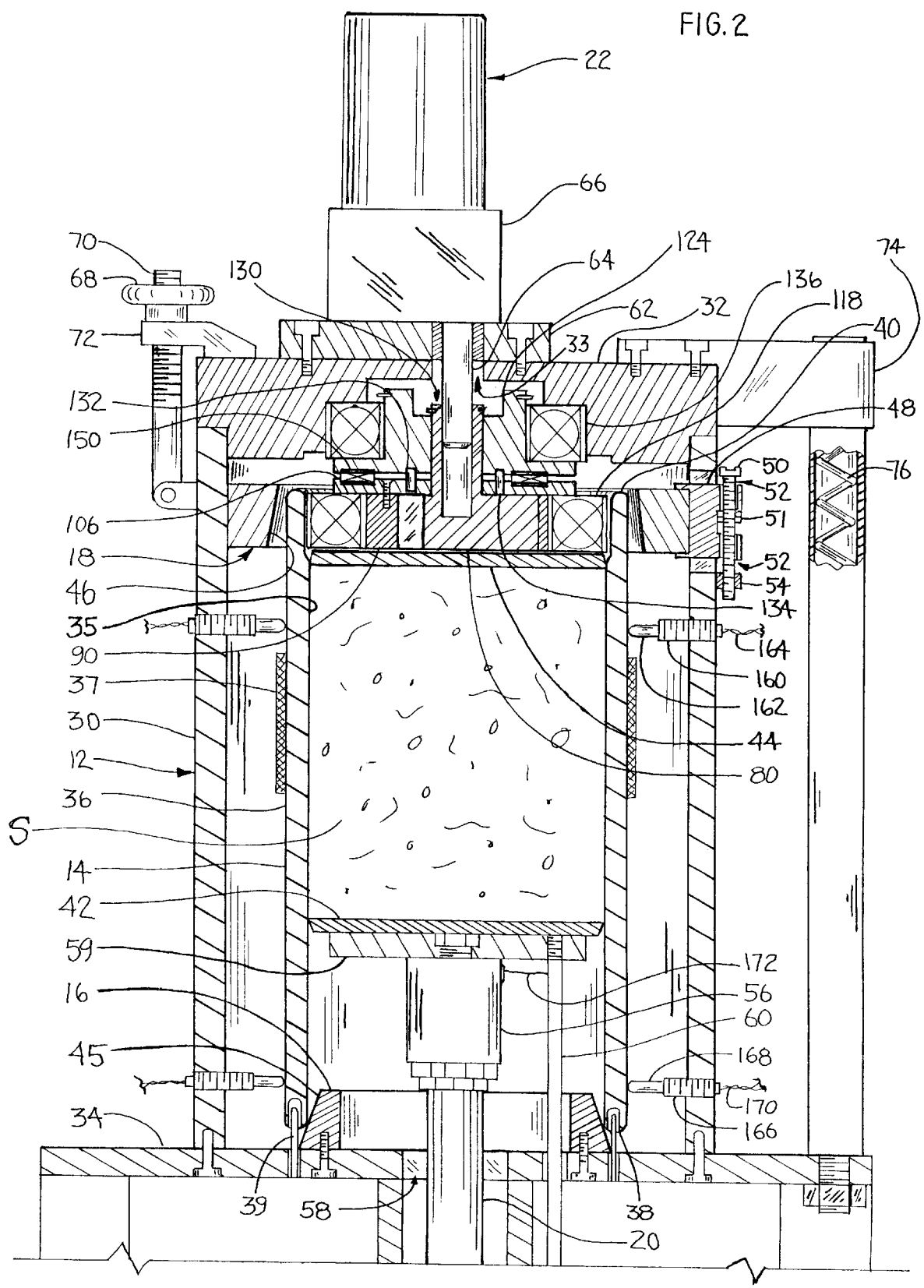
FIG. 2 is a side elevational view and cross section of the upper portion of the embodiment depicted in FIG. 1 with the cross section taken along line 2—2 of FIG. 1.
Figure 3:
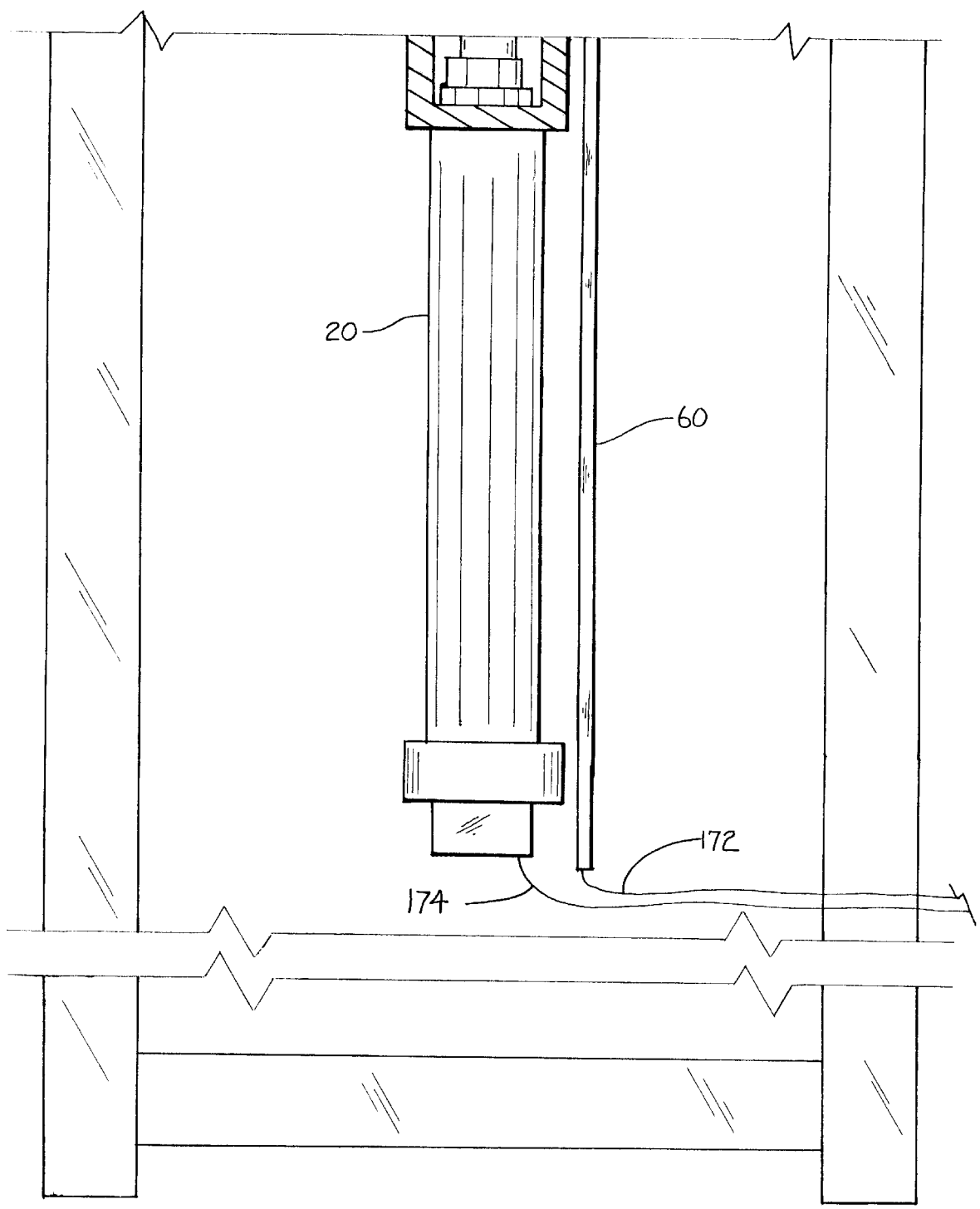
FIG. 3 is a side elevational view of the lower portion of the embodiment depicted in FIG. 1.
Figure 4:
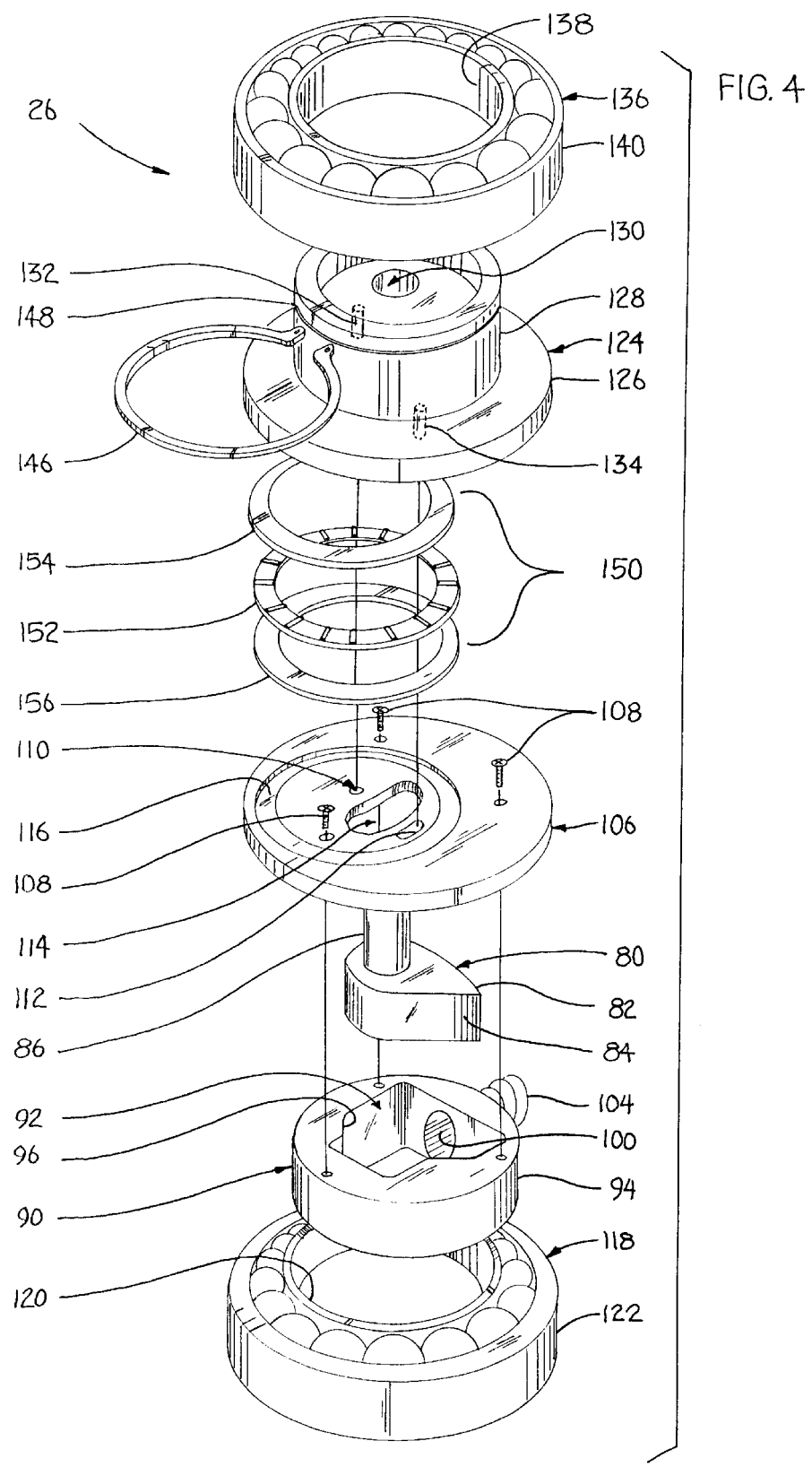
FIG. 4 is an exploded perspective view of a gyratory assembly component of the embodiment of the present invention depicted in FIG. 1.
Figure 5:
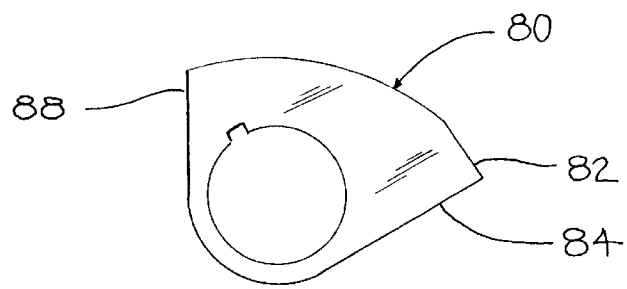
FIG. 5 is a bottom plan view of a gyratory cam component depicted in FIG. 4.

Mold cylinder 14 includes a cylinder wall 36, a mold heater 37, a base plate or first end plate 42, and a sample cap plate or second end plate 44 which as a unit define a test sample volume (sample material S in FIG. 2). Additionally, cylinder wall 36 also includes a rounded first end 38, a rounded second end 40 and an inner surface 35.

First angle rim 16 includes a outer frusto-conical or beveled surface 45 suitable for rolling engagement of cylinder wall 36 at rounded first end 38. First angle rim 16 facilitates aligning cylinder mold 14 to the longitudinal axis of housing wall 30 and motion of rounded first end 38 when cylinder mold 14 is gyrated. When cylinder wall 36 is placed within cylinder housing 12, an additionally secured positioning is achieved when cylinder wall 36 fits over a pair of position index pins 39.

Second angle adjustment rim 18 includes an inner frusto-conical or beveled surface 46. Beveled surface 46 is substantially parallel to beveled surface 45. As used in this sense, parallel should be understood to mean that a plane passing through the centers of first angle ring 16 and second angle adjustment ring 18 and both surfaces 45, 46 will intersect surfaces 45, 46 to produce substantially parallel lines. However, second angle adjustment rim 18 has a greater internal diameter than the outer diameter of first angle rim 16. Beveled surface 46 is suitable for slidable contact engagement of rounded second end 40 of cylinder wall 36 when cylinder wall 36 is tilted in the gyratory mode of operation described hereinbelow.

The distance between first angle rim 16 and second angle adjustment rim 18 is adjustable by suspending second angle adjustment rim 18 in a plurality of adjustment blocks 48. This embodiment of the present invention anticipates the use of three adjustment blocks 48. Adjustment blocks 48 are mounted to housing wall 30 using a screw 50 placed through channel spaces 52 and jam nuts 51 and threading adjustment screw 50 into a mount 54. The plurality of adjustment blocks 48 may be raised or lowered on jam nuts 51 by threading screw 50 in and out of mount 54. Screw 50 has a fine thread to provide for minute changes in the height of adjustment blocks 48 ensuring precise accuracy of tilt for cylinder mold 14. This adjustment means permits the present invention to accept cylinder molds which vary slightly in height, diameter, wall thickness, eccentricity and other characteristics and also compensates for variations in the height, diameter, thickness, eccentricity and other characteristics of the angle rim and the angle adjustment rim as well as to compensate for other variances and tolerances in the construction and assembly of the apparatus.

Hydraulic cylinder 20 includes a cylinder rod 21 ending in a load cell 56 that projects through a housing bottom hole 58 to reach and be mounted to a pressure plate 59 within cylinder housing 12. Hydraulic cylinder 20 and cylinder 21 are in line with the longitudinal axis of cylinder housing 12 and housing wall 30. Compressive forces exerted by hydraulic cylinder 20 are exerted through cylinder rod 21 along the longitudinal axis of housing wall 30. An anti-rotation rod 60 is mounted eccentric on pressure plate 59 and projects back through housing bottom 34 so as to stabilize hydraulic cylinder 20 and cylinder rod 21 against possible rotational forces. Those skilled in the art will recognize that many hydraulic, pneumatic, mechanical, electrical and electromechanical devices are capable of generating the compression force required by the testing procedure and thus are equivalent to the hydraulic cylinder and rod illustrated in the drawings and may be employed in alternative embodiments without departing from the scope and spirit of the present invention.

Motor 22 includes a motor mount adapter plate 62 for adapting a motor to top 32. Additionally, there is a motor gear assembly 66 operably driving a drive shaft 64 extending through a hole 33 centered in top 32 so that drive shaft 64 is centered on and rotates around the longitudinal axis of housing wall 30.

Top 32 is openable and closable using a plurality of lid clamps 68 threaded over a bolt 70 mounted to an outer side wall of housing wall 30 so that lid clamp 68 may slide over and operably engage a lid clamp bracket 72. The present invention anticipates the use of one or more and the present embodiment uses three such lid clamps 68. When opened, top 32 is supported by a lid lift 74 mounted over a lid lift spring 76 of sufficient strength and biased to support the entire weight of top 32 and motor 22, gyratory assembly 26 mounted thereto. Lid lift 74 may be swiveled to swing the entire top 32 away from the upper aspect of housing wall 30.

Gyratory assembly 26 includes a gyratory cam 80, a cam plate 90, a gyratory plate 106, a first angular contact bearing 118, a driven plate 124, and a second angular contact bearing 136. Gyratory cam 80 includes a plunger engaging surface 82, a non-gyratory drive surface 84, a drive shaft sleeve 86, and a gyratory drive surface 88. Drive shaft sleeve 86 is keyed to mount over drive shaft 64.

Cam plate 90 includes a cam housing 92, an outer bearing shaft 94, a gyratory driven surface 96 within cam housing 92, and a non-gyratory driven surface 98 also within cam housing 92. Operably mounted within cam plate 90 is a plunger 100 having a plunger stem 102 operably coupled to a plurality of constant tension spring washers 104 biased to maintain plunger 100 against plunger engaging surface 82 of gyratory cam 80.

Gyratory plate 106 is fixedly mountable to cam plate 90 with a plurality of mounting screws 108. Gyratory plate 106 includes a pivot pin hole 110, a pin slot 112, a clearance hole 114, and a bearing groove 116. Clearance hole 114 provides a space in gyratory plate 106 through which drive shaft sleeve 86 may project.

First angular contact bearing 118 includes an inner bearing race 120 and an outer bearing race 122. Angular contact bearing 118 is mounted over bearing shaft 94 in a friction fit between the surface of bearing shaft 94 and the surface of inner bearing race 120.

Driven plate 124 includes a pin plate 126, a bearing shaft 128, a drive shaft sleeve hole 130, a pivot or gyratory pin 132, and a slot pin 134. Pivot pin 132 and slot pin 134 are fixedly mounted in the under surface of pin plate 126 eccentrically but equal distantly placed from drive shaft sleeve hole 130 which is concentric about the longitudinal axis of housing wall 30. Pin plate 26 and gyratory plate 106 are operably mated through the interaction of a thrust bearing 150 which includes a roller bearing 152 sandwiched between a first bearing race 154 and a second bearing race 156. Thrust bearing 150 is centered about pivot pin 132 to accommodate relative rotational motion of gyratory plate 106 relative to pin plate 126. Each of these bearing races fit within respective bearing grooves with second bearing race 156 nesting within bearing groove 116 of gyratory plate 106. A comparable groove, not seen, in the surface of pin plate 126 is suitable for nesting first bearing race 154. Additionally, pivot pin 132 aligns with pivot hole 110 and slot pin 134 aligns with pin slot 112. Drive shaft sleeve hole 130 has an inner diameter sufficient to accept drive shaft sleeve 86 in slidable but abuttable engagement.

Second angular contact bearing 136 includes an inner bearing race 138 and an outer bearing race 140. Angular contact bearing 136 is placed over bearing shaft 128 and the assembly secured with a C-ring 146 placed within groove 148.

Gyratory compaction control module 24 includes a first mold angle transducer 160, a second mold angle transducer 166, a wire connection 164 to angle transducer 160, a wire connection 170 to angle transducer 166, a load cell wire connection 172, and a cylinder rod position wire connection 174. Angle transducer 160 includes a plunger 162 spring biased so as to continuously rest the tip of plunger 162 against the outer surface of cylinder wall 36. Angle transducer 166 has a similar plunger 168 also spring biased to maintain constant contact between the tip of plunger 168 and the outer surface of cylinder wall 136. Angle transducers 160 and 166 are linearly spaced and in the present embodiment are separated vertically along housing wall 30. Additionally, the present invention anticipates the use of a plurality of pairs of angle transducers spaced sequentially about a cylinder housing 12. The present embodiment utilizes two pairs mounted on opposite sides of housing wall 30 although any number of pairs are feasible.

The function of gyratory assembly 26 is to provide a single roller, i.e., first angular contact bearing 118, to operably engage inner wall 35 proximate rounded second end 40 so that when gyratory assembly 26 is spun in a first direction, first angular contact bearing 118 is concentric about the longitudinal axis of housing wall 30 and no shearing force is applied to sample material S. When gyratory assembly 26 is spun in a second, opposite direction, first angular contact bearing is shifted radially in relation to the longitudinal axis of housing wall 30 by action of gyratory cam 80, tilting the longitudinal axis of cylinder mold 14 in relation to the longitudinal axis of housing wall 30. As gyratory assembly 26 spins in this second direction, first angular contact bearing 118 rolls against inner surface 35 gyrating the axis of cylinder mold 14 about the longitudinal axis of housing wall 30.

The function of driven plate 124 is to counter any lateral moment forces generated from the shearing and compressive forces from cam plate 90, gyratory plate 106 and first angular contact bearing 118 gyrating eccentric to the axis of driven plate 124 which is oriented to the longitudinal axis of housing wall 30 and taking up compressive forces passed through gyratory assembly 26 from hydraulic cylinder 20. These forces are countered by driven plate 124 in conjunction with second angular contact bearing 136 in operable contact with top 32. The result of this effort is to keep second end plate 44 perpendicular to the longitudinal axis of housing wall 30 which maintains the accuracy and reproducibility of tests performed by gyratory compactor apparatus 10. Thrust bearing 150 provides a bearing surface between gyratory plate 106 and driven plate 124 so that gyratory plate 106 may pivot around pivot pin 132 while under compressive forces from hydraulic cylinder 20.

In operation, gyratory compactor apparatus 10 is useful for testing sample material S by subjecting sample material S to compaction and sheer forces secondary to compression of sample S with concurrent gyratory tilting of the specimen container. With top 32 in an open retracted position suspended on lid lift 74, sample material S, such as heated asphalt may be placed into the space defined within cylinder wall 36. Sample cap plate 44 may then be placed on top of material sample S and top 32 centered over cylinder housing 12 to which it can then be clamped securely with lid clamps 68. Mold cylinder 14 is kept at the appropriate temperature using mold heater 37. In the instant example, using heated asphalt the temperature is kept at 300 degrees Fahrenheit.

Sample material S is then initially compacted by controlling cylinder up relay 202 activating cylinder rod drive 200 to bring the pressure, as monitored through load cell 56, up to the testing parameter. In testing asphalt, the approximately 8 pound sample of asphalt is compacted to a pressure of 600 Kpa.

On arriving at this initial compaction pressure, an initial cylinder height measurement is taken which yields an initial density value, since sample volume can be determined from sample height and cross-sectional area. Additionally, this initial density reading may be used to indirectly arrive at the percentage of air voids by knowing the component densities of the rock and bituminous asphalt used in the mixture.

Introduction of shear forces is accomplished through activation of the motor in a clockwise direction which turns cam 80 so as to engage plunger 100 compressing plunger 100 against constant tension spring washers 104, in the preferred embodiment these are a plurality of Bellville washers, pivoting gyratory plate 106 about pivot pin 132 and radially displacing the center of gyratory plate 106 and angular contact bearing 118 off of the longitudinal axis of cylinder housing 12. This displacement of the center of gyratory plate 106 and angular contact bearing 118 displaces the upper end of cylinder wall 36 with them placing a tilt in cylinder wall 36. The degree of tilt imposed on cylinder wall 36 is primarily determined by the amount of radial displacement gyratory plate undergoes. Greater accuracy and reproducibility is possible in conjunction with an adjustable tilting stop such as second angular adjustment rim 18. As gyratory plate displaces radially taking angular contact bearing and cylinder mold 14 with it, when rounded second end 40 reaches beveled surface 46, no further tilting of cylinder mold 14 may occur. Any additional rotation of gyratory cam 80 displacement is taken up by constant tension spring washers 104 being compressed between plunger 100 and inner bearing race 120. Therefore, the firm stop provided by second angle adjustment rim 18 ensures an accurate, reproducible tilt angle. Angular tilt of cylinder wall 36 may be checked by determining the degree of displacement of plungers 162 and 168. By knowing the distance between the plungers, it is then easy to directly calculate the angular tilt. If adjustment is needed, second angular adjustment rim 18 may be raised or lowered as necessary through adjustment of gyratory angular adjustment screw 50 to raise or lower adjustment blocks 48. As mentioned above in the present embodiment three such adjustment blocks 48 with their concomitant height adjustments are used.

Figure 6:
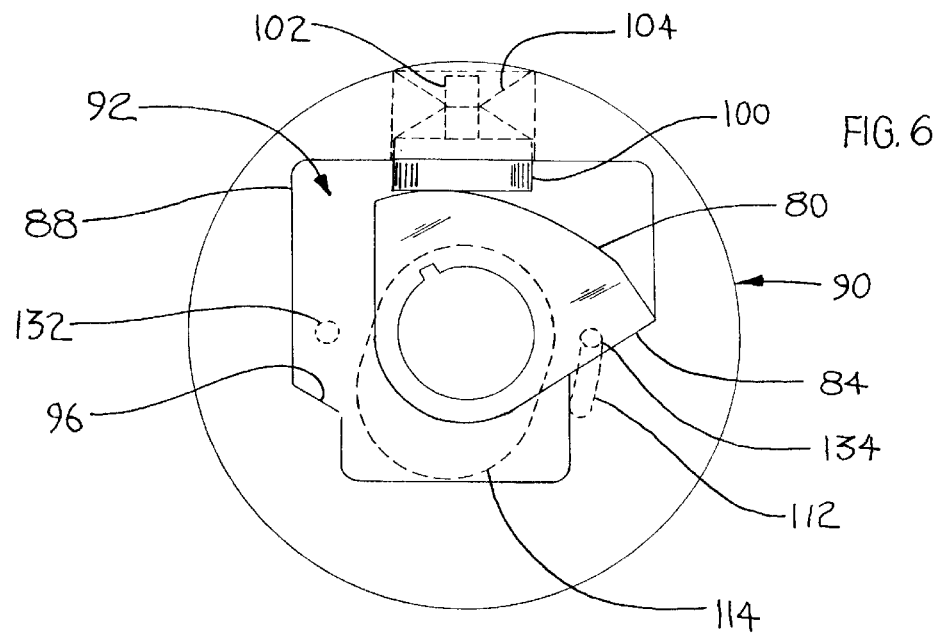
FIG. 6 is a bottom plan view of a cam plate component depicted in FIG. 4, with details of its upper surface and pins of a driven plate shown in phantom.
Figure 7:
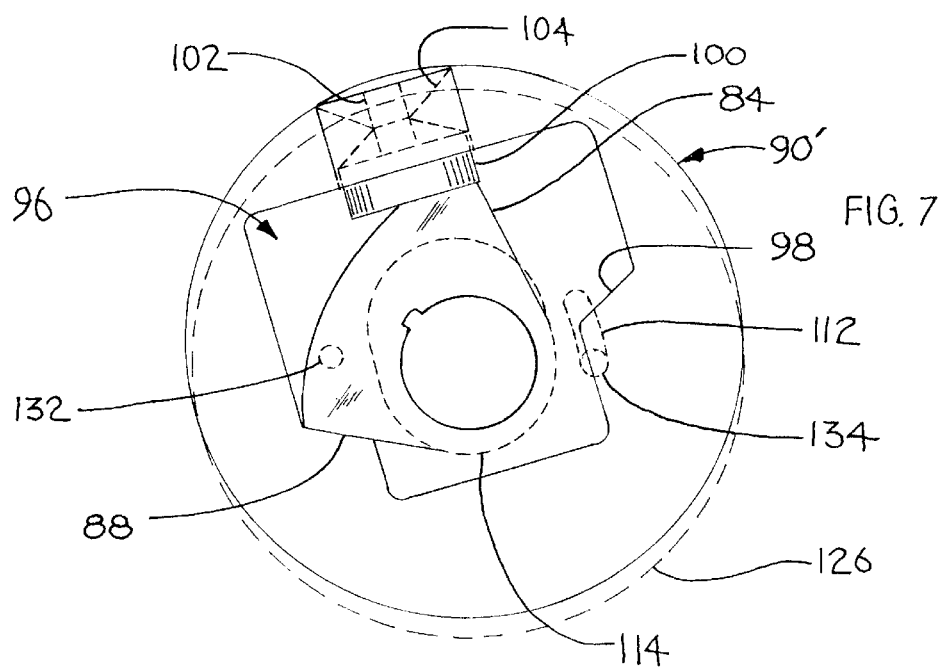
FIG. 7 is a bottom plan view of the depiction shown in FIG. 6 after having spun the gyratory cam to pivot the gyratory plate to its gyratory position relative to the pins of the driven plate.
Figure 8:
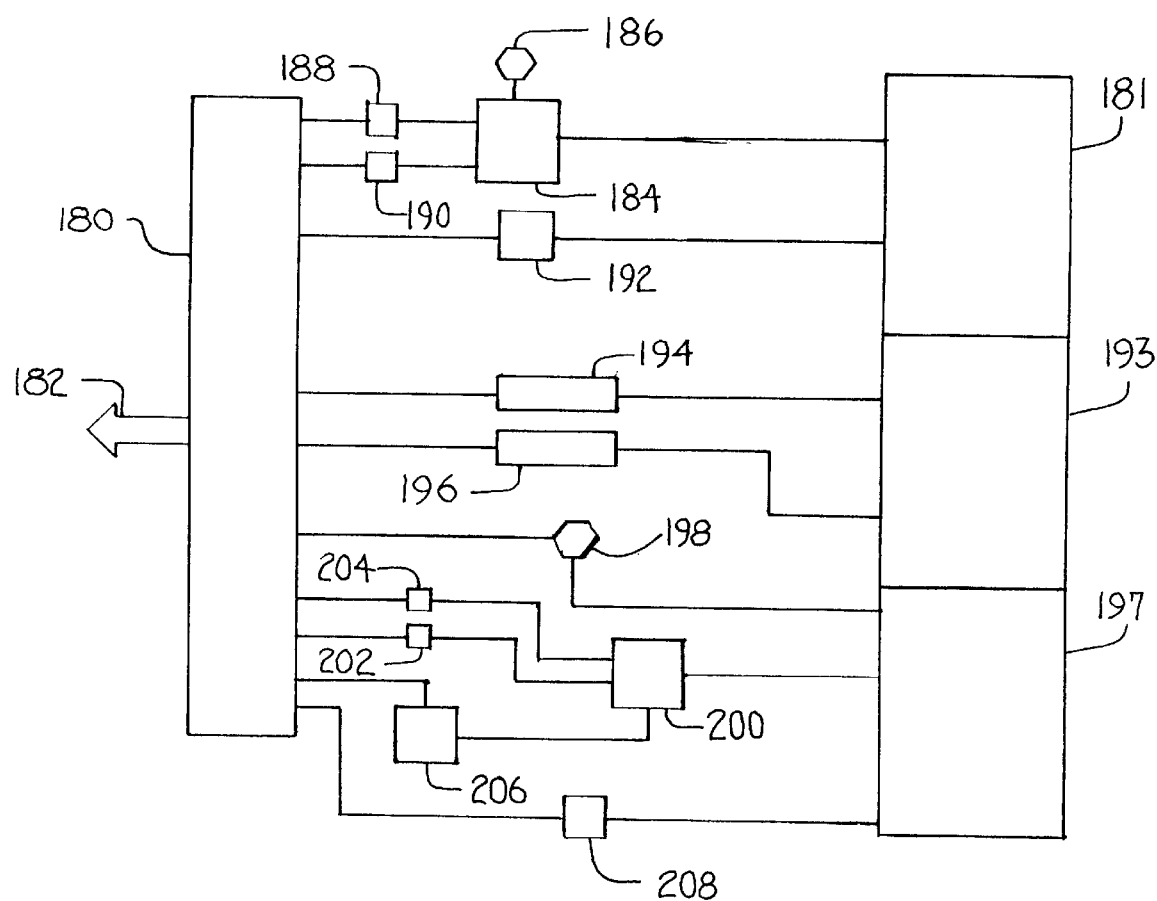
FIG. 8 is a schematic diagram of a gyratory compaction control circuit useful to the embodiment depicted in FIG. 1.

As gyratory cam 80 turns clockwise, as referenced by the motor, eventually gyratory drive surface 88 comes to abut against gyratory driven surface 96 of cam housing 92. At this point in the rotation of gyratory cam 80, the relative motion of gyratory plate 90 in relation to driven plate 124 ceases. This transitioning is represented in reference to FIGS. 6 and 7. In FIG. 6, as viewed from the bottom, gyratory cam 80 is in its non-gyratory position with non-gyratory drive surface 84 intimately contacting non-gyratory driven surface 98 of cam housing 92. In this position, gyratory plate 90 is concentric about the longitudinal axis of cylinder housing 12 and driven plate 124 as represented by the center of drive shaft sleeve 86. Pivot pin 132, slot pin 134, slot 112 and clearance hole 114 are drawn in phantom to better display their positional relationship changes between FIGS. 6 and 7. Additionally, that portion of plunger 100 and plunger stem 102 along with Beltville washers 104 within cam plate 90 are also drawn in phantom.

In turning drive shaft 64 in a clockwise direction, which is a counterclockwise direction as viewed from below in these two Figures, gyratory cam 80 rotates counterclockwise in these views until gyratory drive surface 88 comes into intimate contact with gyratory driven surface 96. During this motion, plunger engaging surface 82 has slid past plunger 100 until it has reached its maximal degree of lift. The motion of gyratory cam 80 relative to plunger 100 causes a pivoting of gyratory plate 90 about pivot pin 132. Secondary to the pivoting of gyratory plate 90 about pivot pin 132, the entire gyratory plate 90 rotates and translates to a new position designated as gyratory plate 90'. Pivot pin 132 and slot pin 112 have remained in place because there has been no motion in driven plate 124 as yet, but as can be seen, pin slot 112 and clearance hole 114 have moved relative to slot pin 134 and drive shaft sleeve 86, respectively. The relative position of driven plate 126 is shown in phantom in FIG. 7.

For a preferred embodiment, the degree of gyratory shift in gyratory plate 90 is 0.25 inches with a total plunger 104 motion of 0.25 inches plus an additional 0.054 inches in order to put a specified load on to the plurality of Bellville washers 104. This degree of eccentricity is used to tilt cylinder wall 36 so as to engage around its second end 40 against second angle adjustment rim 18. For purposes of clarification in the present embodiment, gyratory cam 80 has moved through an arc of approximately 84 degrees and gyratory plate 90 has rotated approximately 17 degrees 30'.

Continued rotation of drive shaft 64 continues to impart rotational motion in gyratory cam 80 which is translated through to cam plate 90 gyrating cam plate 90 about an axis at an angle to the longitudinal axis of drive shaft 64 which is on the longitudinal axis of cylinder housing 12. This continued motion is translated into a gyratory tilting of cylinder wall 36 against second angle adjustment rim 18. End plates 42 and 44 remain perpendicular to the longitudinal axis of cylinder housing 12 and parallel to each other thus imparting a shear force through sample material S as the gyratory tilt moves about and around the longitudinal axis of cylinder housing 12. Thrust forces exerted up through second end plate 44 into cam plate 90 and gyratory plate 106 are translated through thrust bearing 150 into driven plate 124. Any off center moments of force created by the eccentric placement of gyratory plate 90 is counteracted through the relationship of drive shaft sleeve 86 within drive shaft sleeve hole 130 and dissipated through upper angular contact bearing 136 against top 32.

I claim:

1. A gyratory compaction apparatus for creating compression and shear forces in a sample material, the apparatus comprising:
    a hollow cylinder mold open at first and second ends, and including first and second end plates in slidable engagement with an inner surface of the mold proximate respective first and second open ends defining a chamber within the mold between the first and second end plates suitable for receiving the sample material;
    a support frame having a hollow cylindrical interior suitable for receiving the mold therein generally aligned along a support frame longitudinal axis;
    compression means, mountable on the support frame and operably engaging the first end plate, for compressing the sample material within the chamber between the first and second end plates; and
    a gyratory tilt assembly, removably mountable to the support frame proximate the mold second open end and operably engageable with an inner surface of the hollow cylinder mold, comprising:
        rotational drive means for reversibly rotating the gyratory assembly;
        a cam operably attachable to the rotational drive means;
        a gyratory plate having an inner housing for encompassing and operably engaging the cam, the housing having a cam contact surface, a spring biased plunger operably engaging the cam, and a first angle contact bearing for operably engaging the inner surface of the mold proximate the second open end; and
        a driven plate operably engagable between the support frame and the gyratory plate, having a second angle contact bearing operably engaging the support frame concentrically around the support frame longitudinal axis, and operably coupling to the gyratory plate with a pin mounted eccentric to the support frame longitudinal axis and an annular planar thrust bearing concentric to the pin;
    so that when the rotational drive means rotates the cam in a first direction, the cam engages the cam contact surface and the gyratory plate is rotated concentrically about the support frame longitudinal axis, and when the rotational drive means rotates the cam in an opposite second direction, the cam engages the plunger pivoting the gyratory plate about the pin so that the gyratory plate rotates and moves radially in relation to the support frame longitudinal axis rotating eccentrically to the support frame longitudinal axis moving the first angular contact bearing about the inner surface of the mold proximate the second open end tilting the cylinder mold to an angle relative to the support frame longitudinal axis and gyrating the mold about the support frame longitudinal axis while maintaining the angle.

2. The apparatus of claim 1 in which the support frame includes:
    a circular rim concentric to the support frame longitudinal axis and having an outer beveled surface suitable for operably supporting the mold open first end in tiltable engagement; and
    a circular ring adjustably mountable to an inner surface of the support frame concentric to the support frame longitudinal axis having an inner beveled surface suitable for operably engaging the mold open second end.

3. A gyratory compaction apparatus for creating compression and shear forces in a sample material, the apparatus comprising:
    a support frame having a frame longitudinal axis and including a first circular rim with an inner beveled surface and a second circular rim with an outer beveled surface with the first and second circular rims concentric to the frame longitudinal axis;
    a hollow cylinder mold open at a first end and a second end, mountable within the support frame with the second end supportable by, and tiltable on, the second rim beveled surface, the first end suitable for operably engaging the first rim beveled surface, the mold suitable for receiving the sample material therein and having a mold longitudinal axis;
    compression means, mountable on the support frame below the cylinder mold, suitable for compressing the sample material within the mold along the frame longitudinal axis; and
    a gyratory tilt assembly removably mountable to the support frame proximate the mold first end operably engageable with the mold proximate the first end;
    so that when the gyratory tilt assembly operates in a first direction, the mold longitudinal axis is operably placed in alignment with the frame longitudinal axis, and when the gyratory tilt assembly rotates in an opposite direction, the gyratory tilt assembly engages the mold proximate the first end, tilting the first end to engage the first rim beveled surface and tilting the axis of the mold longitudinal axis in relation to the frame longitudinal axis.

4. The apparatus of claim 3 in which the gyratory tilt assembly includes a roller suitable for rollable engagement of an inner surface of the mold.

5. The apparatus of claim 3 in which the mold includes first and second end plates in slidable engagement with an inner surface of the mold.

6. The apparatus of claim 3 in which the compression means includes a hydraulic cylinder and rod.

7. The apparatus of claim 3 further comprising control means for controlling the gyratory assembly and the compression means.

8. The apparatus of claim 3 in which the gyratory assembly includes:

drive means, attachable to the support frame, for reversible rotation of the gyratory assembly;

a cam operably attachable to the drive means;

a roller operably engaging the cam; and a driven plate operably mounted between the support frame and the roller including a pivot pin mounted eccentric to the frame longitudinal axis and engageable with a pin hole in the roller.

9. The apparatus of claim 8 in which the roller includes a spring biased plunger mountable within the roller suitable for operably engaging the cam.

10. The apparatus of claim 8 in which the roller includes a gyratory plate having an inner housing for encompassing the cam and an outer bearing suitable for engaging the mold.

11. The apparatus of claim 8 in which the drive means includes a motor having a drive shaft aligned with the frame longitudinal axis suitable for attachment with the cam.

12. A gyratory compaction apparatus for creating compression and shear forces in a sample material, the apparatus comprising:

a hollow cylinder mold, open at both a first end and a second end, suitable for receiving the material therein, having an inner surface and a mold longitudinal axis;

a support frame, having a frame longitudinal axis, suitable for supporting the mold in a tiltable engagement relative to the frame longitudinal axis;

compression means, mountable on the support frame below the cylinder mold, suitable for compressing the sample material within the mold along the frame longitudinal axis; and a gyratory tilt assembly removably mountable to the support frame proximate the mold first end and having a roller operably engageable circumferentially with the mold inner surface proximate the first end;

so that when the gyratory tilt assembly operates the roller in a first direction, the mold central longitudinal axis is in alignment with the frame central longitudinal axis, and when the gyratory tilt assembly rotates the roller in an opposite direction, the roller rollably engages the inner surface of the mold proximate the mold first end, tilting the mold first end and tilting the axis of the mold longitudinal axis relative to the frame longitudinal axis.

13. The apparatus of claim 12 in which the support frame includes a first circular rim with an inner beveled surface for operably engaging the mold first end and a second circular rim with an outer beveled surface for supporting the mold at the mold second end, with the first and second circular rims concentric to the frame longitudinal axis.

14. The apparatus of claim 12 in which the mold includes first and second end plates in slidable engagement with an inner surface of the mold.

15. The apparatus of claim 12 in which the compression means includes a hydraulic cylinder and rod.

16. The apparatus of claim 12 further comprising control means for controlling the gyratory assembly and the compression means.

17. The apparatus of claim 12 in which the gyratory assembly includes:

drive means, attachable to the support frame, for reversible rotation of the gyratory assembly;

a cam operably attachable to the drive means and operably engageable with the roller; and a driven plate operably mounted between the support frame and the roller including a pivot pin mounted eccentric to the frame longitudinal axis and engageable with a pin hole in the roller.

18. The apparatus of claim 17 in which the roller includes a spring biased plunger mountable within the roller suitable for operably engaging the cam.

19. The apparatus of claim 17 in which the roller includes a gyratory plate having an inner housing for encompassing the cam and an outer bearing suitable for engaging the mold.

20. The apparatus of claim 17 in which the drive means includes a motor having a drive shaft aligned with the frame longitudinal axis suitable for attachment with the cam.

* * * * *